(12) United States Patent
Diakonov et al.

(10) Patent No.: US 6,740,216 B2
(45) Date of Patent: May 25, 2004

(54) POTENTIOMETRIC SENSOR FOR WELLBORE APPLICATIONS

(75) Inventors: Igor Igorevitch Diakonov, Cambridge (GB); Alexander Vladimirovitch Zotov, Moscow (RU); Igor Nikolaevitch Solodov, Moscow (RU); Evgenii Grigorevitch Osadchii, Moscow (RU); Alexander D. Khoteev, Moscow (RU)

(73) Assignee: Schlumberger Technology Corporation, Ridgefield, CT (US)

( * ) Notice: Subject to any disclaimer, the term of this patent is extended or adjusted under 35 U.S.C. 154(b) by 304 days.

(21) Appl. No.: 09/849,059

(22) Filed: May 4, 2001

(65) Prior Publication Data

US 2003/0206026 A1 Nov. 6, 2003

(30) Foreign Application Priority Data

May 18, 2000 (GB) ............................. 0011965

(51) Int. Cl.⁷ ...................... G01N 27/333; G01N 27/40
(52) U.S. Cl. .................... 204/418; 204/416; 204/435
(58) Field of Search .................... 204/435, 416, 204/418, 419

(56) References Cited

U.S. PATENT DOCUMENTS

| | | | |
|---|---|---|---|
| 3,410,779 A | * | 11/1968 | Whitehead et al. |
| 3,780,575 A | | 12/1973 | Urbanosky |
| 3,859,851 A | | 1/1975 | Urbanosky |
| 4,018,660 A | * | 4/1977 | Hansen et al. |
| 4,273,639 A | * | 6/1981 | Gottermeier |
| 4,415,858 A | | 11/1983 | Hale |
| 4,818,366 A | * | 4/1989 | Yonco et al. |
| 4,861,453 A | * | 8/1989 | Matsuoka et al. |
| 4,994,671 A | | 2/1991 | Safinya et al. |
| 5,005,406 A | | 4/1991 | Jasinski et al. |
| 5,351,532 A | | 10/1994 | Hager |
| 5,445,228 A | | 8/1995 | Rathmell et al. |
| 5,489,371 A | * | 2/1996 | Joseph et al. |
| 5,517,024 A | | 5/1996 | Mullins et al. |
| 5,518,590 A | | 5/1996 | Fang |
| 5,736,650 A | | 4/1998 | Hiron et al. |
| 5,829,520 A | | 11/1998 | Johnson |
| 6,023,340 A | | 2/2000 | Wu et al. |

FOREIGN PATENT DOCUMENTS

| | | |
|---|---|---|
| DE | 42 25 904 A1 | 2/1993 |
| JP | 2087059 | 6/1990 |
| WO | 99/00575 | 1/1999 |
| WO | 99/56120 A1 | 11/1999 |

OTHER PUBLICATIONS

Diakonov, I. I., Pokrovski G. S., Schot J., Castet S., and Gout R. J–C. "An experimental and computational study of sodium—aluminum complexing in crustal fluids" in Geochim. Cosmochim. Acta 60(1996), 197–211.

Midgely D. "A review of pH measurement at high temperature" Talanta 37(1990) 8, 767–781.

Solodov I. N., Velichkin, V. I. Zotov, A. V. et al "Distribution and geochemistry of contaminated subsurface waters in fissured volcanogenic bed rocks of the Lake Karachai area, Chelyabinsk, South Urals" Lawrence Berkeley Laboratory Report 36780/UC–603 (1994b) RAC–6, Ca, USA.

(List continued on next page.)

*Primary Examiner*—Alex Noguerola
(74) *Attorney, Agent, or Firm*—William L. Wang; William B. Batzer; John J. Ryberg (57) ABSTRACT

A potentiometric sensor for wellbore applications having a permanent aqueous contact between measuring and reference electrode, whereby contact is ensured by discharging the internal solution from the reference electrode directly onto a measuring (ion-sensitive) membrane and protecting the reference junction of the reference electrode with water wet porous material, such as sintered glass. It is advantageously applied to oil-water mixtures under high pressure and/or temperature.

16 Claims, 9 Drawing Sheets

OTHER PUBLICATIONS

Bates, R. G. (1964) Determination of pH. Theory and practice. John Wiley, NY. Chapter 9 (1973).

Ives D.J. and Janz G.J. (1961) Reference electrodes: Theory and Practice. Academic Press New York, 127pp. Chapter 8–10.

Disteche A. (1959) pH measurements with a glass electrode withstanding 1500 kg/cm2 hydrostatic pressure. Review Sci. Instr., 30, 6, 474–478.

Disteche A. (1962) Electrochemical measurements at high pressures. J. Electrochem. Soc., 109, 11, 1084–1092.

Disteche A and Disteche S (1967) The effect of pressure on the dissociation of carbonic acid from measurements with buffered glass electrode cells. J. Electrochem. Soc., 114, 330–340.

Ross, J.W., Riseman, J.H., and Krueger J.A. (1973). Potentiometric gas sensing electrodes. Applied chemistry, 36, 473–486.

Culberson C. and Pytkowicz R.M. (1968) Effect of pressure on carbonic acid, boric acid, and the pH in seawater. Limnol. Oceanogr., 13, 3, 403–417.

Brand M.J. and Rechnitz G.A. (1970) Differential potentiometry with ion–selective electrodes. A new instrumental approach. Anal. Chem., 42, 616–622.

Crolet J.L. and Bonis M.B. (1983) pH measurements in aqueous CO2 solutions under high pressure and temperature. Corrosion, 39, 2, 39–46.

Pokrovski G.S., Zotov A.V., Sergeev A.S., Gout R., and Schott J. (1993) New glass electrodes for pH measurements in aqueous solutions up to 200° C *Proc. 4th Int. Symp. on Hydrothermal Reactions,* Nancy, 189–192.

Pokrovski G.S., Schott J., and Sergeev A.S. (1995) Experimental determination of the stability constants of $NaSO_4^-$ and $NaB(OH)_4^0$ in hydrothermal solutions using a new high–temperature sodium–selective glass electrode—Implications for boron isotopic fraction. *Chemical Geology,* 124, 253–265.

Pokrovski G.S., Schott J., Harrichoury J.–C., and Sergeev A.S. (1996) The stability of aluminum silicate complexes in acid solutions from 25 to 150° C. *Geochim. Cosmochim. Acta,* 60, 2495–2501.

Fournier, P. Oelk rs, E. H. Gout, R. Pokrovski, G. (1998) Experimental determination of aqueous sodium–acetate dissociation constants at temperature from 20 to 240C. Chemical Geology, 151, 1–4, 69–84.

Ostvold T. and Kaasa B. (1998) Prediction of pH and mineral scaling in waters with varying ionic strength containing $CO_2$ and $H_2S$ for $0<T(C)<200$ and $1<P(bar)<500$. In Proceedings, $4^{th}$ Intl. Symp. Advances in Solving Oilfield Scale. Aberdeen, Jan. 1998.

Niedrach L (1980) Oxygen ion conducting ceramics: A new application in high temperature–high pressure pH sensors. Science 207, 1200–1202.

Niedrach L. (1980) A new membrane–type pH sensor for use in high temperature–high pressure water. J. Electrochem. Soc. 127, 2122–2130.

Niedrach L. (1982) Use of a high temperature pH sensor as a "Pseudo–reference electrode" in the monitoring of corrosion and redox potentials at 285C. J. Electrochem. Soc. 129, 7, 1445–1449.

Niedrach L. W. and Stoddard H. (1984) Development of a high temperature pH electrode for geothermal fluids. J. Electrochem. Soc. 131, 5, 1017–1026.

Lvov, S. N. Zhou, X. Y. Macdonald, D. D (1999) Flow–through electrochemical cell for accurate pH measurements at temperatures up to 400C. J. Electroan. Chem., 463, 2, 146–156.

Lvov, S. N. Gao, H. Kouznetsov, D. Balachov, I. Macdonald, D. D. (1998) Potentiometric pH measurements in high subcritical and supercritical aqueous solutions. Fluid Phase Equilibria, 150/151, 515–523.

Lvov, S. N Gao, H. Macdonald, D. D. (1998) Advanced flow–through external pressure–balanced reference electrode for potentiometric and pH studies in high temperature aqueous solutions, J. Electroan. Chem., 443, 2, 186–194.

Kriksunov, L. B., Macdonald D.D (1995) Corrosion in Supercritical Water Oxidation Systems: A Phenomenological Analysis. J. Electrochem. Soc. 142, 12, 4069–4073.

Macdonald, D. D. Kriksunov, L. B. Millett, P. J. (1994) Development and Testing of Combination pH Sensing Electrodes for Use at High Temperatures and Pressures. Extended abstracts, Electrochemical Soc., 2, 276–277.

Kriksunov, L. Macdonald, D. D. Millett, P. J. (1994) Tungsten/Tungsten Oxide pH Sensing Electrode for High Temperature Aqueous Environments. J. Electrochem. Soc. 141, 11, 3002.

Macdonald D. D. Hettiarachchi S, Song H, Makela K, Emerson R and Benhaim M (1992) Measurement of pH in subcritical and supercritical aqueous systems. J Sol Chemistry 21, 8, 849–881.

Macdonald D. D., Hettiarachchi S and Lenhart S (1988) The thermodynamic viability of ytrria–stabilized zirconia pH sensors for high temperature aqueous solutions. J. Sol. Chem. 17, 8, 719–732.

Hettiarachchi S, Kedzierzawski P and Macdonald D. D. (1985) pH measurements of high temperature aqueous environments with stabilized–zirconia membranes. J Electrochem. Soc. 132, 8, 1866–1870.

Tsuruta T. and Macdonald D. D. (1982) Stabilized ceramic membrane electrodes for the measurement of pH at elevated temperatures. J. Electrochem. Soc. 129, 6, 1221–1225.

Ding K and Seyfried W. E., Jr. (1997) Application and stability of YSZ pH sensor in high temperature hydrothermal fluids. Proc. of the Fifth International Symposium on Hydrothermal Reactions., Galtinburg, Tennessee, USA, Jul. 20–24, 145.

Ding, K. and Seyfried, W. E. (1996) Direct pH Measurement of NaCI–Bearing Fluid with an in Situ Sensor at 400C and 40 Megapascals. Science, 5268, 1634–1635.

Bourcier W. L., McKibben M. A. and Barnes H. L. (1983) Hydrothermal pH and $H_2$ measurements using the zirconia electrode and Teflon membrane. Proc. of the 4th International Symposium on Water–Roch Interaction, Misasa, Japan, 59–61.

Bourcier W. L, Ulmer G C., Barnes H. L. (1987) Hydrothermal pH of $ZrO_2$, Pd hydrides and Ir oxides. In: Hydrothermal Experimental Techniques (ed. G. S. Ulmer and H. L. Barnes) Chap. 7, 157–188. Wiley–Interscience.

Light T. S. and Fletcher K. S. (1985) Evaluation of the zirconia pH–sensor at 95° C. Analyt. Chem. Acta. 175, 117–126.

Inda Y, Yamashita K., Umegaki T., and Greenblatt M. (1996) High temperature pH sensitivities of stabilized zirconia and ceria ceramics. Solid Stat Ionics, 86–88, 1121–1124.

Buzzanca G., Ronchetti C., and Uberti F. (1986) Probe for pH measurements at high temperature. Proceedings, $2^{nd}$ Intl. Conf. On On–line Surveillance and Monitoring, Venise, Italy, May 1986, 271–286.

Dobson J.V., Firman R.E., and Thirsk H.R. (1971) The behavior of cells using silver/silver chloride and skin-–calomel electrodes at temperatures from 25 to 200C and 1 bar to 2 kbar pressure. Electrochimica Acta, 16, 793–809.

Danielson M. J. (1979) Th construction and thermodynamic performance of an Ag—AgCl reference electrode for use in high temperatur aqueous environments containing $H_2$ and $H_2S$. Corrosion, 35, 5, 200–204.

Agarwal A.K. and Staehle R. W. (1977) A silver—silver chloride reference electrode for the hifh temperature and high pressure electrochemistry. Corrosion, 33, 11 418–419.

Vermilyeva D.A. and Indig M.E. (1972) J. Electrochem. Soc., 119, 39.

Indig M.E. and Nelson J.L. (1991) Electrochemical measurements and modelling predictions in boiling water reactors under various operating conditions. Corrosion, 47, 3, 202–209.

Munro, W.A. Thomas, C.L.P. Simpson, I. Shaw, J. Dodgeson, J. (1996) Deterioration of pH Electrode Response Due to Biofilm Formation on the Glass Membrane. *Sensors and Actuators* B37, pp187–194.

Davis R.D. (1973) A major step toward self–maintenance of pH electrodes. Instrumentation in the food and beverage industry. 2, 83–86.

Wakeman R. (1986) Electrofiltration: microfiltration plus electrophoresis. The Chemical Engineer, Jun. 1966, 65–70.

Manheim F. (1961) In situ natural measurements of pH and Eh in natural waters and sediments. Stockholm Contr. Geol., 8, 27–36.

Ben–Yaakov S. and Kaplan I.R. (1968) High pressure pH sensor for oceanographic applications. Rev. Sci. Instr., 39, 8, 1133–1138.

Ben Yaakov S. and Kaplan I.R. (1968) pH–Temperature profiles in ocean and lakes using an in situ probe. Limnol. Oceanogr., 13, 688–693.

Ben–Yaakov S. and Kaplan I.R. (1968) A versatile probe for in situ oceanographic measurement. J. Oceanogr. Technol., 2,3, 25–29.

Whitfield M. (1971) A compact potentiometric sensor of novel design. In situ determination of pH, $pS^{2-}$ and Eh. Limnol. Oceanogr., 16, 829–837.

Bolviken B., Logn O., Breen A., Uddu O. (1972) Instrument for in situ measurements of Eh, pH and self–potentials in diamond drill holes. Proceedings of $4^{th}$ Geochem. Explor. Symp. London Apr. 17–20, 1972.

Liden J., Ginstrup O., and Ingri N. (1980) A probe for the measurement of pH and pe in situ in natural water systems. Chemica Scripta, 15, 203–205.

Seers K.J. (1983) An instrument for simultaneous measurement of Eh and pH in boreholes. BMR J. Austr. Geology and Geoph., 8, 89–91.

Solodov I.N et al. (1993) Technogenic oxidation change to uranium bearing sandstones. *Litologiya/Poleznie Iskopaemie*, 6, 84–96 (in Russian).

Solodov I.N., Zelenova O.I. and G.A. Shugina (1994a) Technogenic geochemical barriers in the ore–bearing horizons of uranium hydrigenic deposits. *Geokhimiya*, 3, 415–432 (in Russian).

Solodov, I.N., Khoteev, A.D., Chertok, M.B. and V.A.Zadvomov. (1997) Geochemistry of natural and contaminated underground waters in the area of surface and underground storages of liquid radioactive wastes (Chelyabinsk and Tomsk oblasts of Russia). Proceedings of the International Conference on Radioactive Waste Management and Environmental Remediation, 1997, vol. 6, pp. 737–742.

Solodov, I.N., Zotov A.V., Khoteev A.D., Mukhamet–Galeev A.P., Tagirov B.R., and Apps J.A. (1998) Geochemistry of natural and contaminated subsurface waters in fissured bed rocks of the Lake Karachai area, Southern Urals, Russia. Applied Geochemistry, 1998, vol. 13; No. 8, pp. 921–940.

Solodov, I. N. (1998) The retardation and attenuation of liquid radioactive waste due to the geochemical properties of the zone of injection. Special Publication—Geological Society of London, 1998, vol. 128, pp. 265–280.

Hydrolab DataSonde 4 and Minisonde Multiprobes. Hydrolab Corp. Web site: http://www.hydrolab.com/html/series4a.htm#datasonde4a, see also.

Greenspan MiniSonde—CS302. Greenspan Technology Pty Ltd. Web site: http://www.greenspan.com.au, see http://www.greenspan.com.au/_data/page/3956/CTDP1200–SP.PDF, Mar. 25, 2002.

Aquilina L., Cecile J.L., Sureau J.F., and Degranges P. (1993) WELCOM (Weil Chemical On–line–monitoring) I. Technical and economic aspects. Scientific Drilling, 5, 5–12.

Sureau J.F., Fritz B., and Aquilina L. (1993) Diagraphie et sulvi geochimiques des fluides en cours de forage. Resultats preliminaires du forage Balazuo–1, Ardeche. Programme Geologie Profonde de la France. C.R. Acad. Sci, Paris, 316, Serie II, 349–356.

Aquilina L., Brach M. (1995) Characterization of Soultz hydrogeochemical system: welcom (weil chemical on–line monitoring) applied to deepening of GPK–1 borehole. Geotherm. Sol. Technol., 4, 4, 239–251.

Aquilina L., Eberschweiler C., and Perrin J. (1996) Comparison of hydrogeochemical logging of drilling fluid during coring with results from geophysical logging and hydraulic testing. Example of Morte–Merie scientific borehole, Ardeche–France, Deep Geology of France Programme. J. Hydrol., 185, 1–21.

Jasinski, R. Efird, K.D. (1988) Electrochemical Corrosion Probe for High Resistivity Hydrocarbon/Water Mixtures. *Corrosion,* 44, No. 9, pp658–663.

Heath S.M. and Pritchard A.M. (1995) On–line chemical sensing technology for downhole and topside monitoring in produced brines. Advances in solving oilfield scaling. Conf. Abstr., Aberdeen, Nov. 21–22, 1995.

Shorthouse G. and Peat B. (1996) Downhole chemical sensors for sub–sea oil wells. Material Science News, 2, 12–13.

Snieckus D. (1999) Tipping the scales. Offshore Engineer, Sept. 1999, p117.

Craston D.H., Jones C.P., and Williams D.E. (1991) Microband electrodes fabricated by screen printing process: applications in electroanalysis. Talanta, 38, 1, 17–26.

English statement 1.

English statement 2.

English statement 3.

English statement 4.

* cited by examiner

Fig. 1
(Prior Art)

Reference electrode - keeping fixed potential

New sensor design for MDT

- Insert mini Probe into new sampling module
- Water-only analysis

POTENTIOMETRIC SENSOR FOR WELLBORE APPLICATIONS

The invention relates to a chemical sensor tool for use in downhole analyzing of fluids produced from subterranean formations. More specifically it relates to a potentiometric sensor for downhole pH and ion content analysis of effluents produced from subterranean formation

BACKGROUND OF THE INVENTION

Analyzing samples representative of downhole fluids is an important aspect of determining the quality and economic value of a hydrocarbon formation.

Present day operations obtain an analysis of downhole fluids usually through wireline logging using a formation tester such as the MDT™ tool of Schlumberger Oilfield Services. However, more recently, it was suggested to analyze downhole fluids either through sensors permanently or quasi-permanently installed in a wellbore or as through sensor mounted on the drillstring. The latter method, if successful implemented, has the advantage of obtaining data while drilling, whereas the former installation could be part of a control system for wellbores and hydrocarbon production, therefrom.

To obtain an albeit crude estimate of the composition of downhole fluids, the MDT tools uses an optical probe to estimate the amount of hydrocarbons in the samples collected from the formation. Other sensors use resistivity measurements to discern various components of the formations fluids.

Particularly, knowledge of downhole formation (produced) water chemistry is needed to save costs and increase production at all stages of oil and gas exploration and production. The following applications are of interest:

Prediction and assessment of mineral scale and corrosion;

Strategy for downhole oil/water separation and water reinjection;

Understanding of reservoir compartmentalization/flow units;

Characterization of water break-through;

Derivation of $R_w$.

Some chemical species dissolved in water (like, for example, $Cl^-$ and $Na^+$) do not change their concentration when removed to the surface either as a part of a flow through a well, or as a sample taken downhole. Consequently information about their quantities may be obtained from downhole samples and in some cases surface samples of a flow. However, some chemical species, such as $H^+$(pH=-log[concentration of $H^+$]) $CO_2$, $H_2S$ and water parameters, such as ORP (redox potential or Eh), do change significantly while trip to the surface. This change occurs mainly due to a huge difference in temperature and pressure between downhole and surface environment. In case of sampling, this change may also happen due to degassing of a sample (seal failure), mineral precipitation in a sampling bottle, and (especially in case of $H_2S$)—a chemical reaction with the sampling chamber. It should be stressed that pH, $H_2S$, $CO_2$, and ORP are among the most critical parameters for corrosion and scale assessment. Consequently it is of considerable importance to have their downhole values precisely known.

Hence, there is and will continue to be a demand for downhole chemical measurements. However, no downhole chemical measurements actually performed in an oil and gas producing well have been reported so far.

To meet demand for chemical measurements of increasing accuracy, it may appear obvious to adapt chemical analysis tools known from chemical laboratory practice to the hostile environment of a subterranean borehole. Such known analysis tools include for example the various types of chromatography, electrochemical and spectral analysis. Particularly, the potentiometric method has been widely used for the measurements of water composition (pH, Eh, $H_2S$, $CO_2$, $Na^+$, $Cl^-$ etc. . . . ) both in the laboratory and in the field of ground water quality control. However, so far the environmental conditions within a subterranean wellbore rendered attempts to perform such measurements under real hydrocarbon wellbore condition purely theoretical.

Among the known state of the art in the field of high temperature potentiometric are: Diakonov I. I., Pokrovski G. S., Schott J., Castet S., and Gout R. J. -C. "An experimental and computational study of sodium—aluminum complexing in crustal fluids", in: *Geochim. Cosmochim. Acta,* 60(1996), 197–211 and Midgley D. "A review of pH measurement at high temperatures", in: Talanta, 37(1990), 8, 767–781.

General downhole measurement tools for oilfield applications are known as such. Examples of such tools are found in the U.S. Pat. Nos. 6,023,340; 5,517,024; and 5,351,532 or in the International Patent Application WO 99/00575. An example of a probe for potentiometric measurements of ground water reservoirs is published as: Solodov, I. N., Velichkin, V. I., Zotov, A. V. et al. "Distribution and Geochemistry of Contaminated Subsurface Waters in Fissured Volcanogenic Bed Rocks of the Lake Karachai Area, Chelyabinsk, Southern Urals" in: Lawrence Berkeley Laboratory Report 36780/UC-603(1994b), RAC-6, Ca, USA.

It is therefore an object of the present invention to provide apparatus and methods to perform potentiometric measurements in a subterranean wellbore for hydrocarbon exploration and production.

SUMMARY OF THE INVENTION

The invention achieves its objects by providing a potentiometric sensor with at least one reference and one measuring electrode having a permanent aqueous contact between measuring and reference electrode. The contact is preferably ensured by discharging the internal solution from the reference electrode directly onto a measuring (ion-sensitive) membrane and protecting the reference junction of the reference electrode with water wet porous material, such as sintered glass.

In a preferred embodiment, the stability of a signal/electrode fouling can be checked by measuring a signal with and without an additional resistance.

A potentiometric technique can be applied for example as part of a production logging tool and open hole formation tester tool (Modular Dynamic Tester, MDT). In the latter case, the technique can provide a downhole real-time water sample validation or downhole pH and $H_2S$ measurements for prediction of mineral scale and corrosion assessment. A new gas sensing combination potentiometric sensor is also proposed for simultaneous detection of $H_2S$ and $CO_2$ partial pressures in any fluid (oil, gas, water).

These and other features of the invention, preferred embodiments and variants thereof, possible applications and advantages will become appreciated and understood by those skilled in the art from the following detailed description and drawings.

BRIEF DESCRIPTION OF DRAWINGS

FIGS. 5A, B illustrate variants of a potentiometric sensor in accordance with the present invention;

FIG. 6 shows a self-discharging reference electrode for use as part of a potentiometric sensor in accordance with the present invention;

DETAILED DESCRIPTION OF THE INVENTION

The theory of potentiometry and its application to water measurements at ambient temperatures are well developed. The method is based on the measurement of electromotive force (e.m.f., or E) in a potentiometric cell which consists of measuring and reference electrodes (half-cells).

Figure 1:
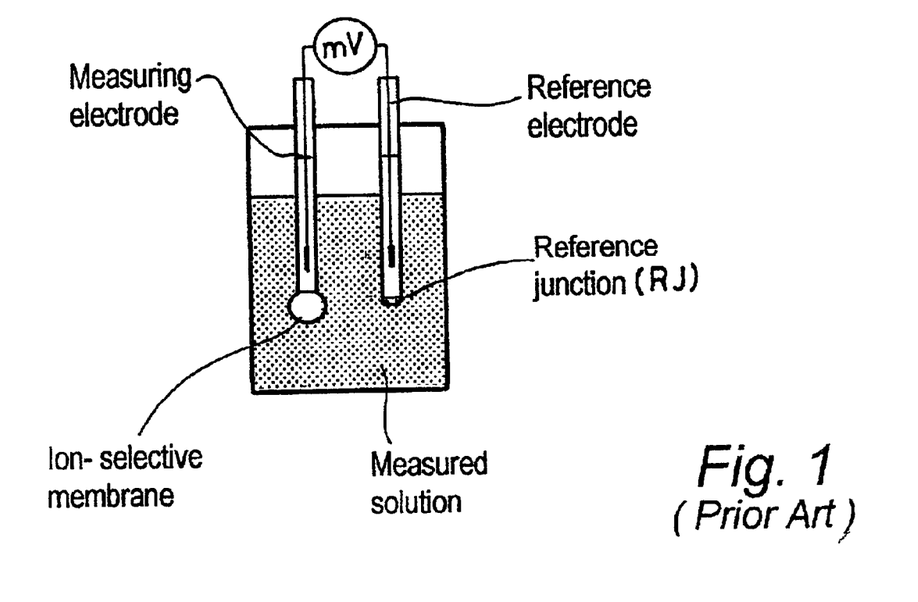
FIG. 1 shows a schematic diagram of the main elements of a known potentiometric sensor.

FIG. 1 shows the general components of a known potentiometric cell. A measuring electrode is inserted into a solution. This electrode consists of an internal half element (for example, Ag wire covered by an AgCl salt) in a solution of a fixed pH (for example, 0.1M HCl in some pH electrodes), and an ion-selective membrane (like glass $H^+$ selective membrane in pH glass electrode). The reference electrode also contains an internal half-element (typically the same AgCl;Ag) inserted in a concentrated KCl (for example 3M) solution/gel saturated with $Ag^+$, which diffuses (or flows) through the reference (liquid) junction.

Figure 2:
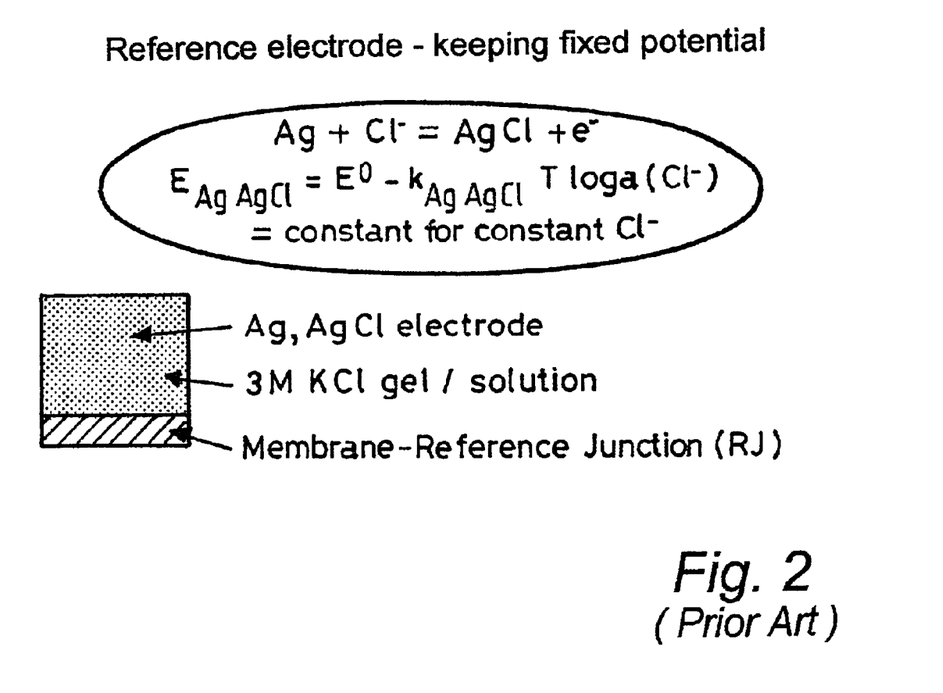
FIG. 2 shows details of a reference electrode of a known potentiometric sensor.

Details of the reference electrodes are shown in FIG. 2: A reference electrode contains an internal half-element (typically AgCl;Ag) inserted in a concentrated KCl (for example 3M) solution/gel saturated with $Ag^+$, which diffuses (or flows) through the reference (liquid) junction, thus maintaining electrical contact. The potential of this electrode is fixed at a constant temperature as chloride ion concentration inside is a constant. It is important that the membrane (RJ) should stay intact (no clogging/fouling) and consequently (b) there should aqueous continuum between measuring and reference electrode.

The ion-selective electrode measures the potential that arises because of the difference in concentrations of a corresponding ion ($H^+$ in case of pH) in the internal solution and in the measured solution. This potential is measured against the reference potential on the reference electrode, which is fixed because of a constant composition of a reference solution/gel (see FIG. 2). Electrodes may be separate (separate half cells), and combined into one ("combination electrode").

The measuring electrode has a special sensitive ion-selective membrane. The membrane potential is related to the activity (concentration) of a given ion in a solution. The reference electrode has a constant potential (see FIG. 2). The measured e.m.f. (E, potential difference) is an overall a function of the temperature and the activity of an ith ion, to which the measuring electrode is selective:

$$E=E^0+(k*T)*\log(a_i), \qquad [1]$$

where E is the measured electromotive force (e.m.f.) of the cell (all potentials are in V), $a_i$ corresponds to the activity of the ith ion and is proportional to its concentration. $E^0$ is the standard potential (at temperature T) corresponding to the E value in a solution with the activity of ith ion equal to one. The term in parenthesis is a so-called Nernstian slope for the plot of E as a function of $\log(a_i)$. This slope (or the constant "k") together with the cell (electrode) constant ($E^0$) is experimentally determined via a calibration procedure using standard solutions with known activities of ith ion. For good quality undamaged electrodes this slope should be very close to the theoretical one, equal to $(R*T/F*z)$, where F is the Faraday constant (23061 cal/mole), R is the gas constant (1.9872 cal/mole K), $z_i$ is the charge of ith ion. The schematic design of a potentiometric cell is shown in FIG. 1 above. Note that potentiometric electrodes may be used as separate entities (separate, individual electrodes, or half-cells) or be assembled in a "combination" electrode (like very popular pH combination glass electrode).

Figure 3:
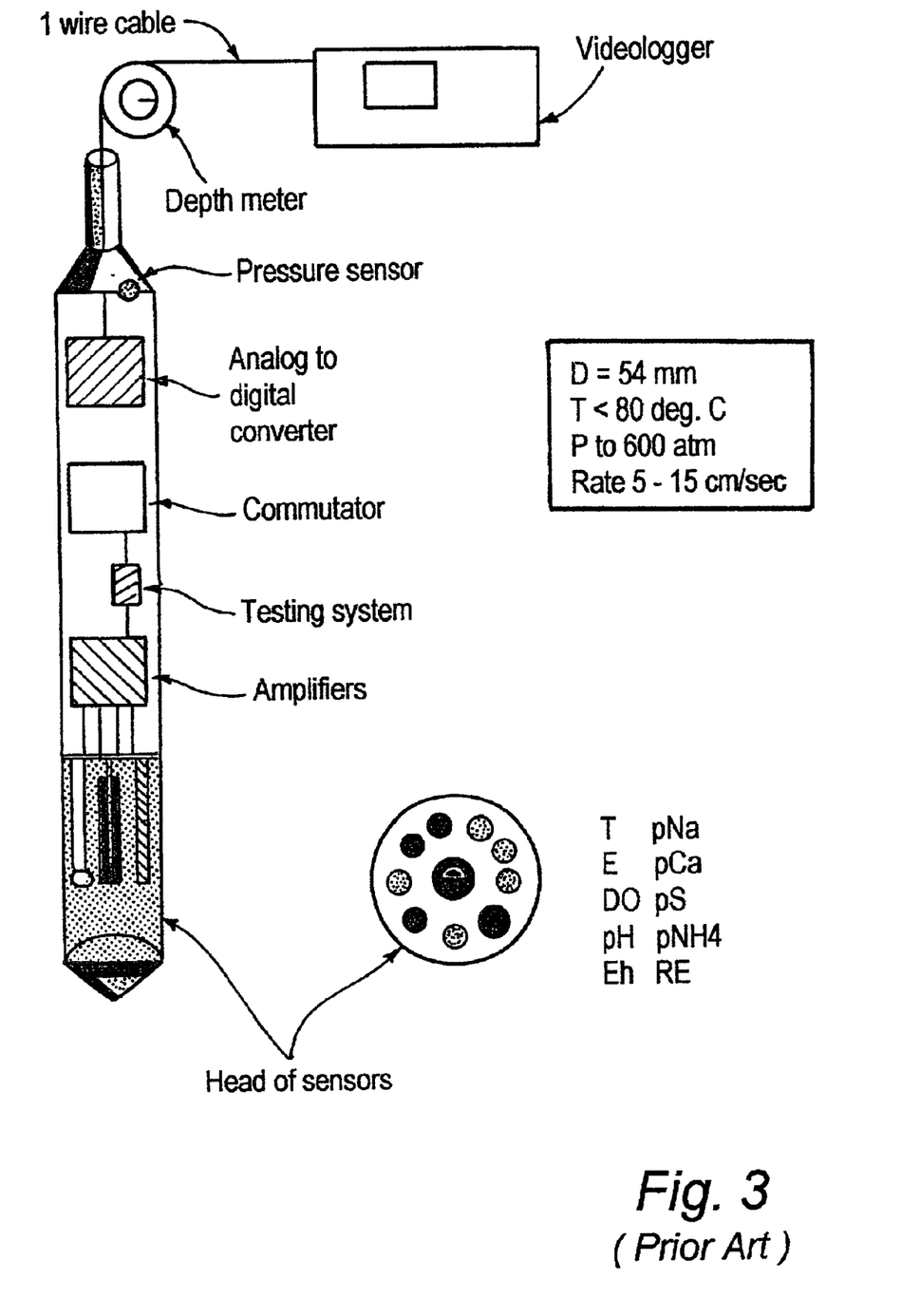
FIG. 3 shows a schematic diagram of a downhole probe of a known potentiometric sensor.

In FIG. 3, there are schematically illustrated elements of a known downhole analyzing tool as used by Solodov et al (see background). Potentiometric electrodes are located at the bottom part of the probe and include those for pH, Eh (or ORP), $Ca^{2+}$ (pCa), $Na^+$ (pNa), $S^{2-}$ (pS), $NH_4^+$ ($pNH_4$), and reference electrode (RE). $H_2S$ partial pressure may be calculated from pH and pS readings.

In the follow major aspects of the invention are described in detail. These aspects cover three main areas:

The adaptation of potentiometric method to measurements in oil/water mixtures including oil-continuous phase Use of the method in downhole tools Design of a new gas-sensing combination electrode for the simultaneous detection of $CO_2$ and $H_2S$ partial pressures A first aspect relates to the adaptation of potentiometric method to measurements in oil/water mixtures including oil-continuous phase.

Such Potentiometric measurements are feasible under two conditions:

Firstly, the membranes (measuring and RJ) should stay intact without clogging or fouling. The second condition is to provide an aqueous continuum between measuring and reference electrode.

It was found that glass and silver sulfide membranes are not prone to immediate fouling by oil and its components. Consequently, in this invention devices are used which eliminate fouling or clogging of the reference junction (RJ) of the reference electrode. Simultaneously with eliminating RJ fouling these devices help to establish a stable aqueous contact between measuring and reference electrodes thus allowing stable measurements in oil continuous phase. Some of the proposed devices also decrease fouling of the ion-sensitive membranes of the measuring electrodes.

All of the above is achieved by using a passive water-wet protection layer on the reference junction, The protection layer is manufactured from special porous water wet materials (for example, a sintered glass frit). When used in combination electrodes with glass/silver sulfide (or similar) membranes which are not very prone to fouling, this device enables measurements until glass membrane fouling occurs as it does not protect the measuring electrode.

By adding an induced discharge of the reference solution/gel directly onto measuring membrane of the measuring (ion-selective) electrode, a closed electrical circuit is created even in water-in-oil emulsions. This procedure may be applied in conjunction with the use of the above-described water-wet protective cap. In combination, discharge and cap allow measurements in oil continuous phase (maintaining water layer on measuring surface and RJ) and simultaneous membrane cleaning by an induced discharge of reference fluid. This reference fluid may also clean the membrane of the measuring electrode.

Figure 4:
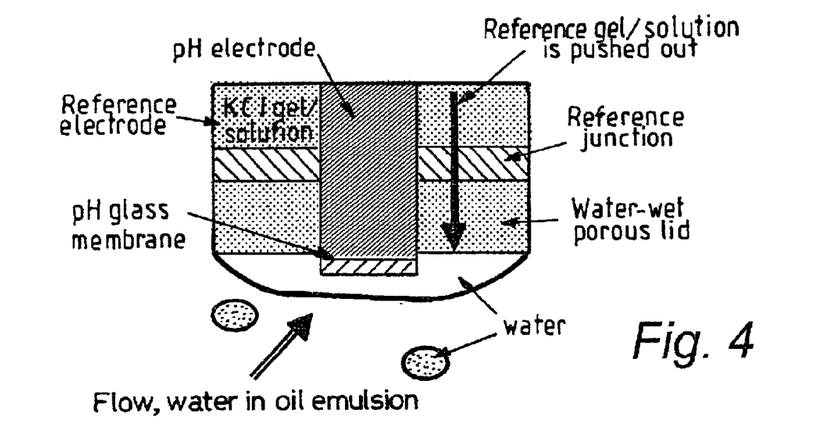
FIG. 4 shows a schematic diagram of the main elements of an example of a potentiometric sensor in accordance with the present invention.

FIG. 4 shows a combination pH electrode consists of pH glass electrode and an enveloping reference electrode. Reference electrode has a protective water-wet cap on the reference junction. The cap is made from sintered glass. This material may or may not itself be saturated with the reference gel. A protective water-wet cap ensures a constant presence of a water continuous layer on the surface of the cap and consequently a closed circuit with the measuring glass pH membrane. KCl gel/solution either diffuses through the cap, or is pushed through via various means to ensure electrical contact. The water present in water-in-oil emulsion exchanges with the water in a surface layer on top of this sensor. Consequently, the measurement accounts for any change in the effluent passing the sensor (see FIG. 4).

Figures 5A, 5B, 6:
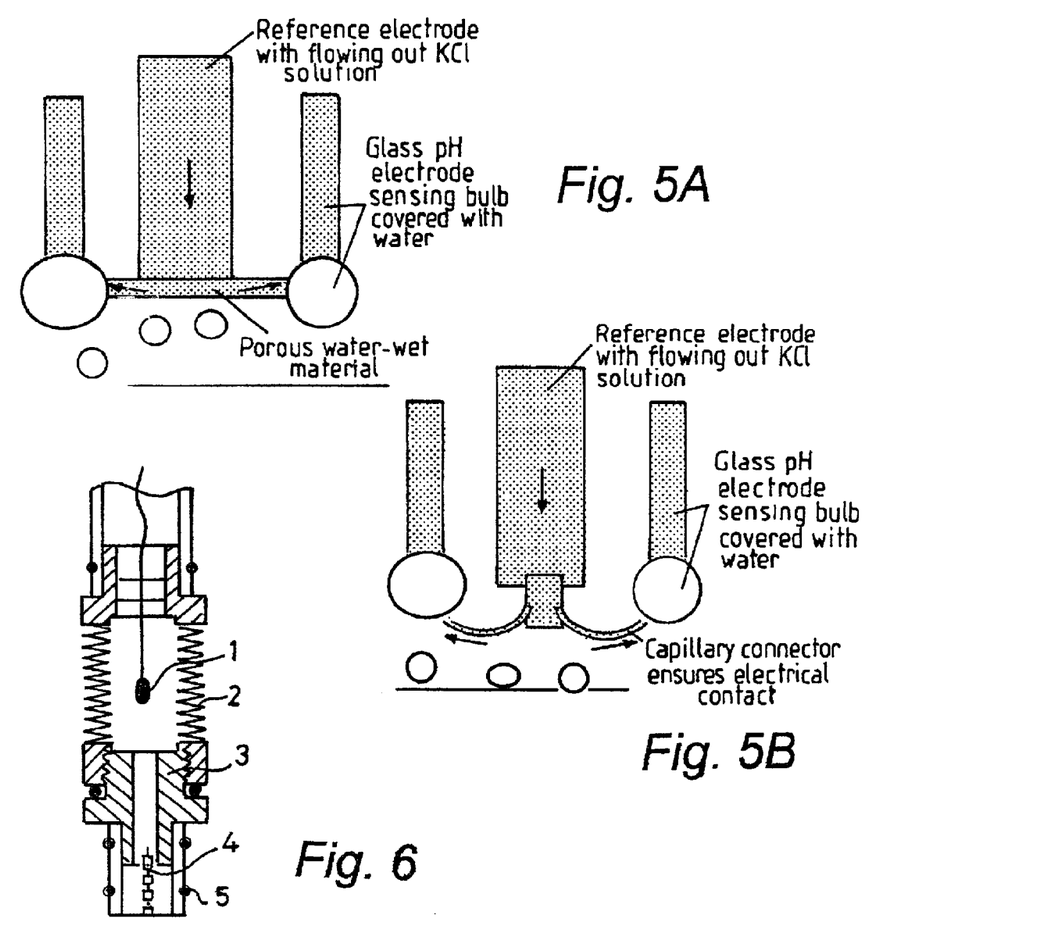

In FIGS. 5A and 5B there are shown two variants having a separate reference and measuring electrodes. The measuring glass membrane of pH electrode is water-wet. An electrical contact in water-in-oil emulsions is assured via a direct discharge of a reference solution/gel onto a surface of the measuring membrane. This is achieved either via diffusion (or induced flow) through a water-wet protective cap (e.g. a sintered glass disc) (FIG. 5A) or through a capillary contact (FIG. 5B). The reference solution/gel may be pushed out from the reference electrode via various means.

Direct discharge of reference solution/gel is achieved via pushing it out of the reference electrode with the help of
  a piston;
  a load, placed on top of an inflatable chamber filled with reference solution;
  a buoyancy system, where a floating chamber is filled with a light gas is placed underneath a flexible chamber filled with the reference solution. Consequently, this floating chamber exert a pressure onto a flexible tank with a reference fluid; or variants or combinations thereof.

A self-discharging type reference electrode is shown in FIG. 6. The reference electrode may be filled with aqueous solution (usually KCl), gel, or solid electrolyte (or it may contain a solid micro-porous matter saturated with an aqueous solution or gel). The induced discharge of the reference electrolyte establishes an aqueous electrical contact with the measuring electrode. The discharge itself is achieved using a self-compressing deformable reference electrode (2). A flexible bag (2) is charged in a stretched state. The bag is then closed by a gland (3) having a central passage filed with a micro-porous medium (4). The elastic force compresses the bag and pushes solution out through the medium (4). In this design, neither the rate nor time of solution outflow may be controlled.

Figure 7:
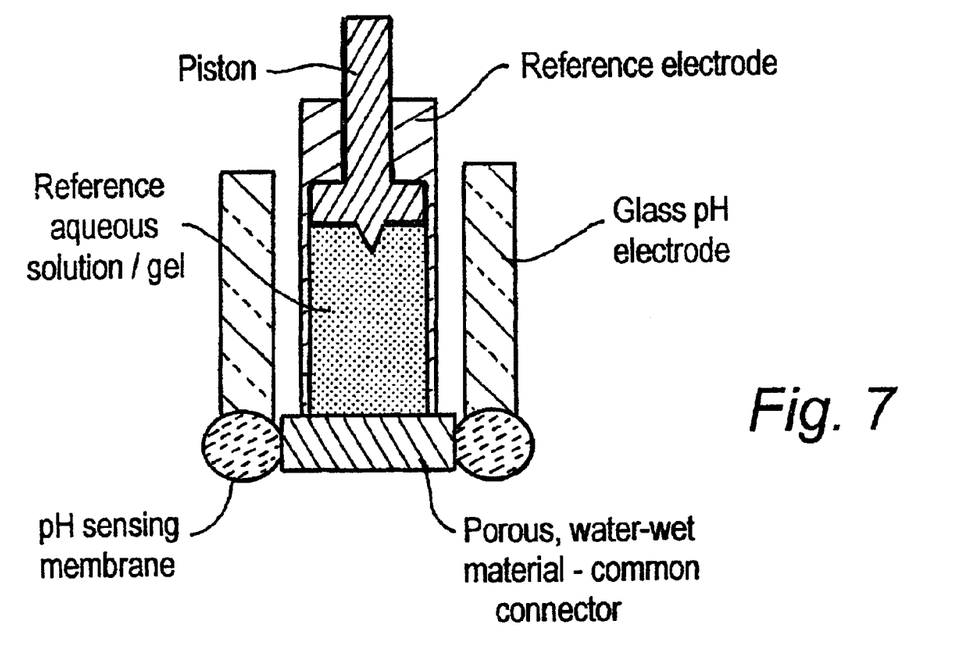
FIGS. 7, 8 illustrates further variants of discharging electrodes.
Figure 8:
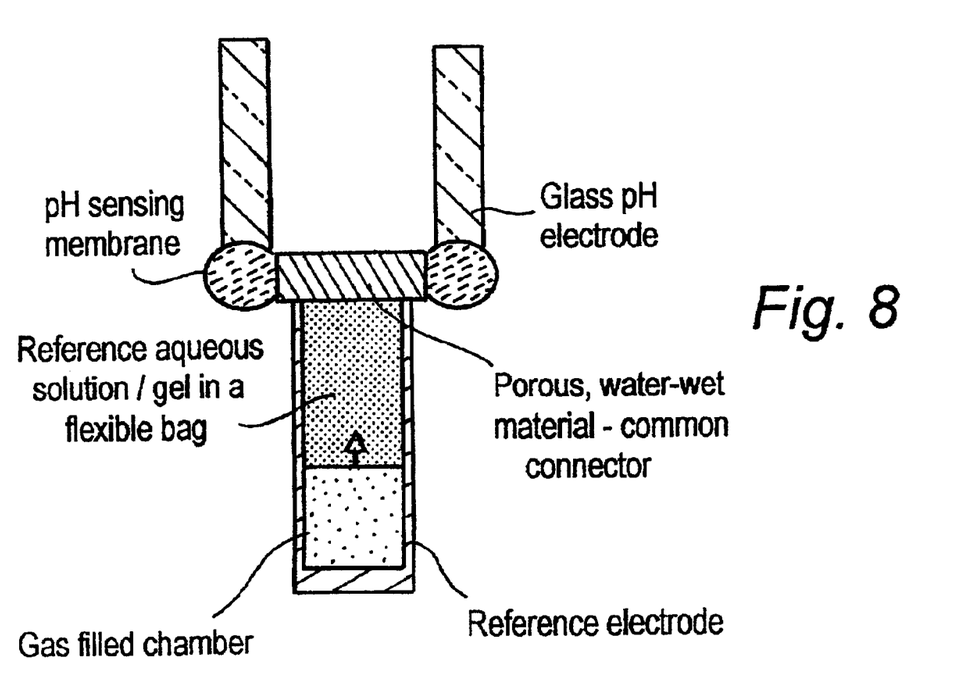

Further examples of discharge type reference electrodes are shown in FIGS. 7 and 8.

The electrode of FIG. 7 comprises a piston exerting a pressure onto an inner chamber of the reference electrode. The chamber is filled with the reference aqueous solution or gel. The porous water-wet material of the cap ensures an electrical contact to the pH sensing membranes. In operation the piston can be driven by an external motor or hydraulic system.

In the variant of FIG. 8, a gas-filled chamber replaces the piston of FIG. 7. The reference solution is stored in a flexible bag.

Figure 9:
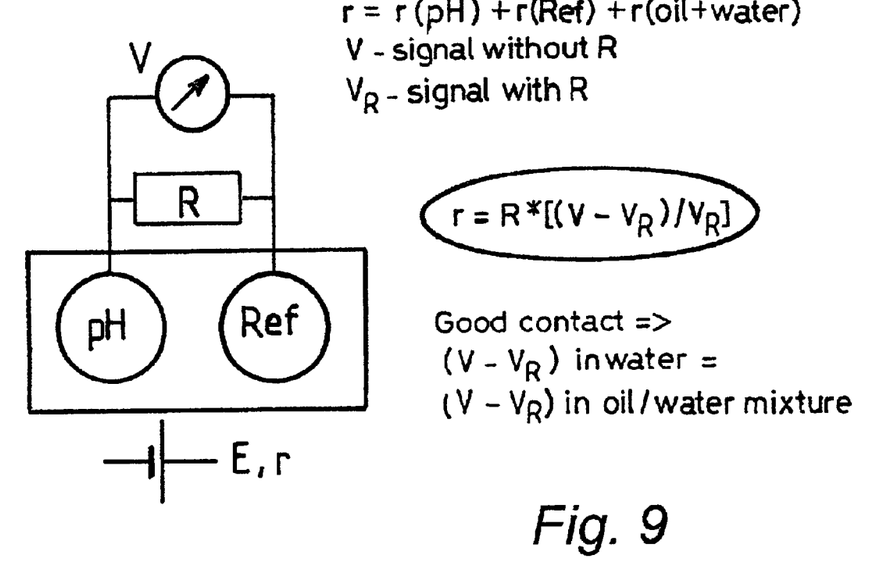
FIG. 9 illustrates a further variant of an analyzing tool as part of a permanently installed flow monitoring unit in a wellbore.

The above sensor design can be improved by an internal measurement against a known resistor as shown in FIG. 9. An additional resistance "R" placed between the measuring and reference electrodes will enable a check for electrical contact quality to be carried out. The electrode pair may be regarded as a battery with its internal resistance "r". This internal resistance is caused by electrodes and the measuring solution.

The resistance of the glass electrodes is very high (>10 Mohm), whereas the resistance of the pure aqueous solutions (no oil) and the reference electrode (Ag, AgCl) is very small compared to the resistance of the glass electrodes. The resistance of oil may be comparable to that of the glass electrodes. Consequently, when the space between the electrodes fills with oil, the oil forms a fouling film on their surfaces, the overall resistance of a cell increases and the signal changes. Measuring this cell resistance with the help of a reference measurement performed employing an additional resistance "R" indicates the quality of the electrical contact. A condition for a good electrically conductive circuit is a stable, constant voltage drop when the additional resistance is switched on.

Figure 10:
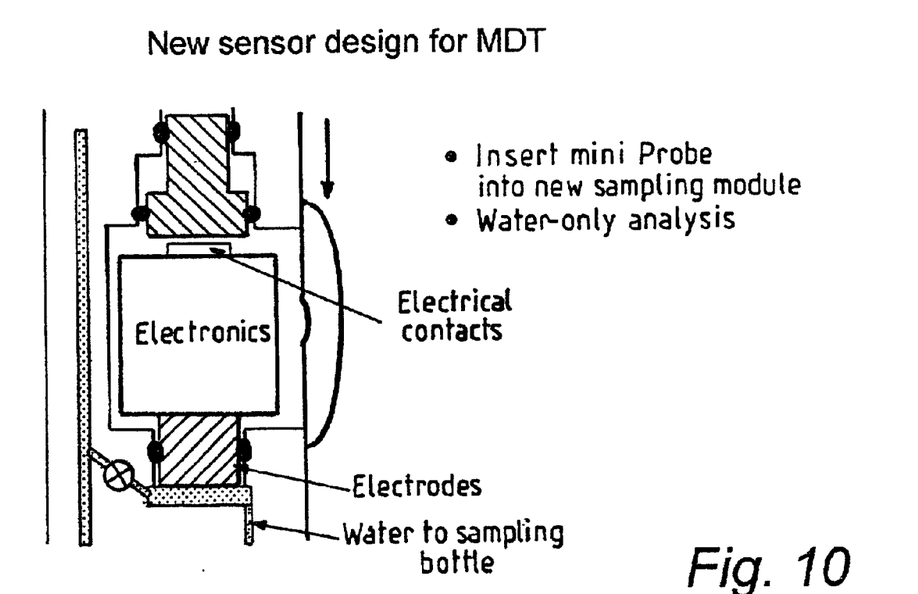
FIG. 10 shows a compact potentiometric probe of particular use for a downhole application, in accordance with the invention.

A compact potentiometric probe of particular use for a downhole application is shown in FIG. 10. The probe may be placed inside the module body (shown) or inside a sampling bottle. A system of valves, flow lines and additional chambers (not shown) ensures the contact of the probe's sensors with the sample effluent. This system may also supply calibration and cleaning solutions downhole.

Figure 11:
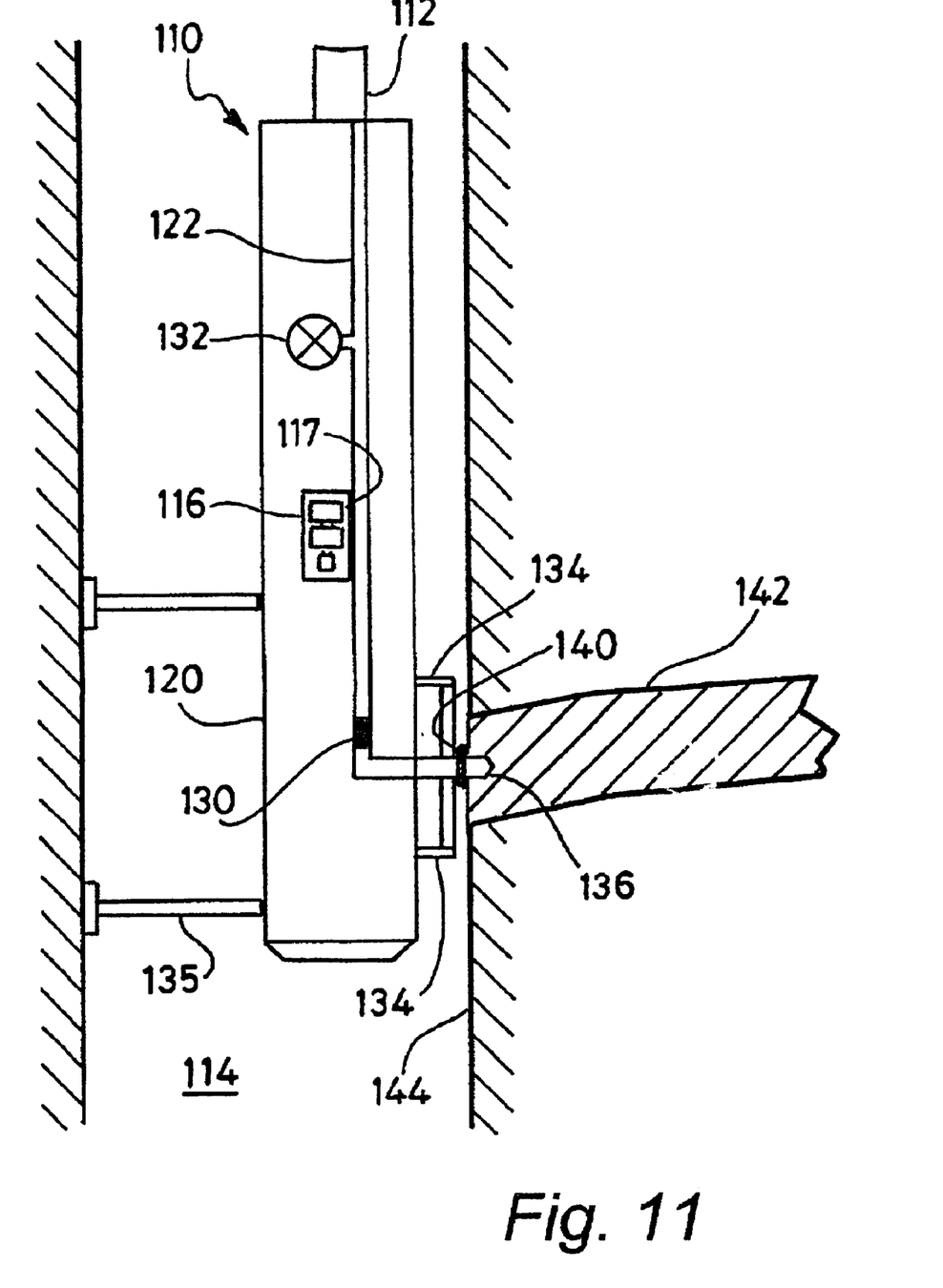
FIG. 11 shows a formation testing apparatus held on a wireline within a wellbore, in accordance with the invention.
Figure 12:
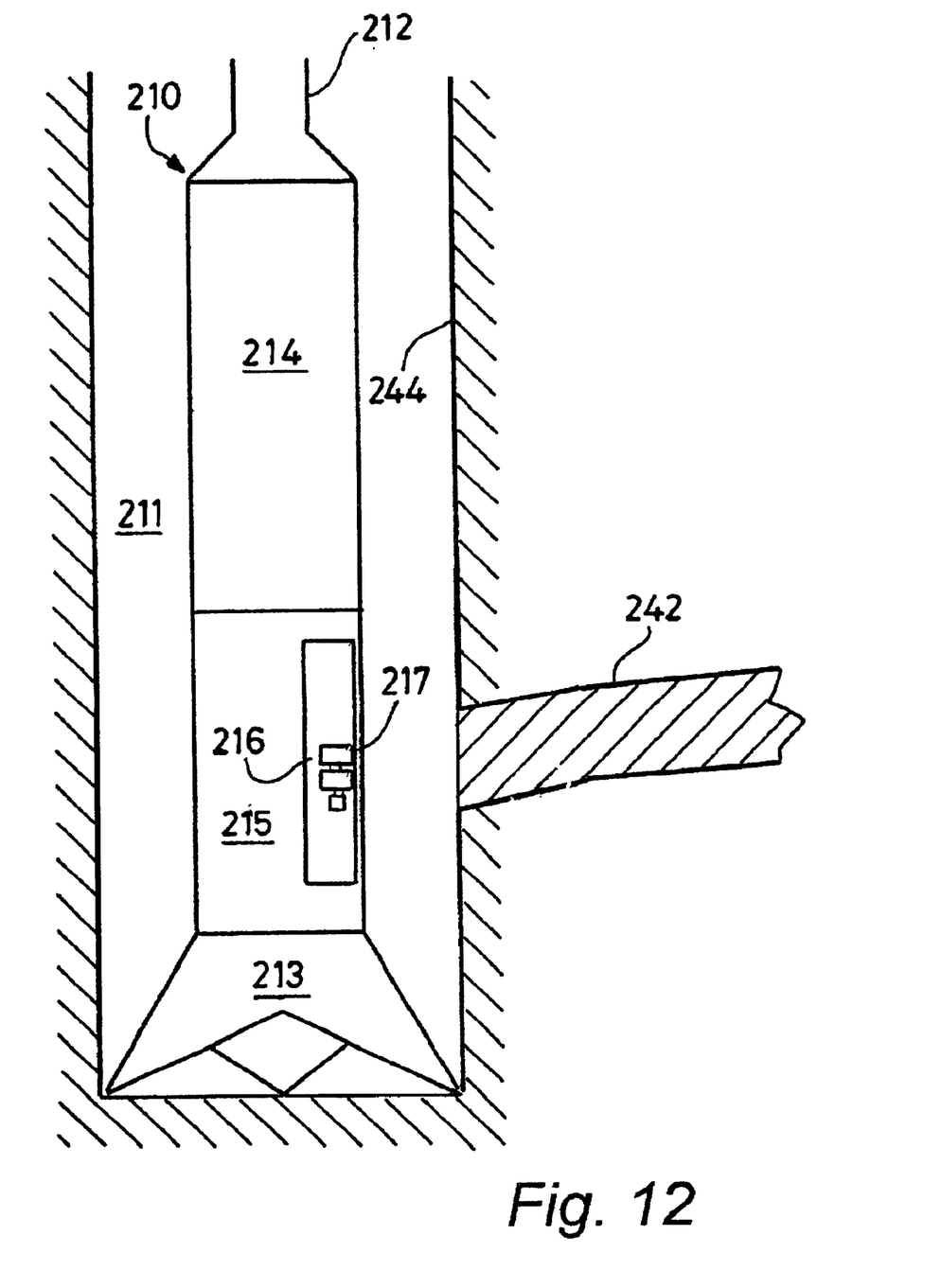
FIG. 12 shows a wellbore and the lower part of a drill string including the bottom-hole-assembly, in accordance with the invention.
Figure 13:
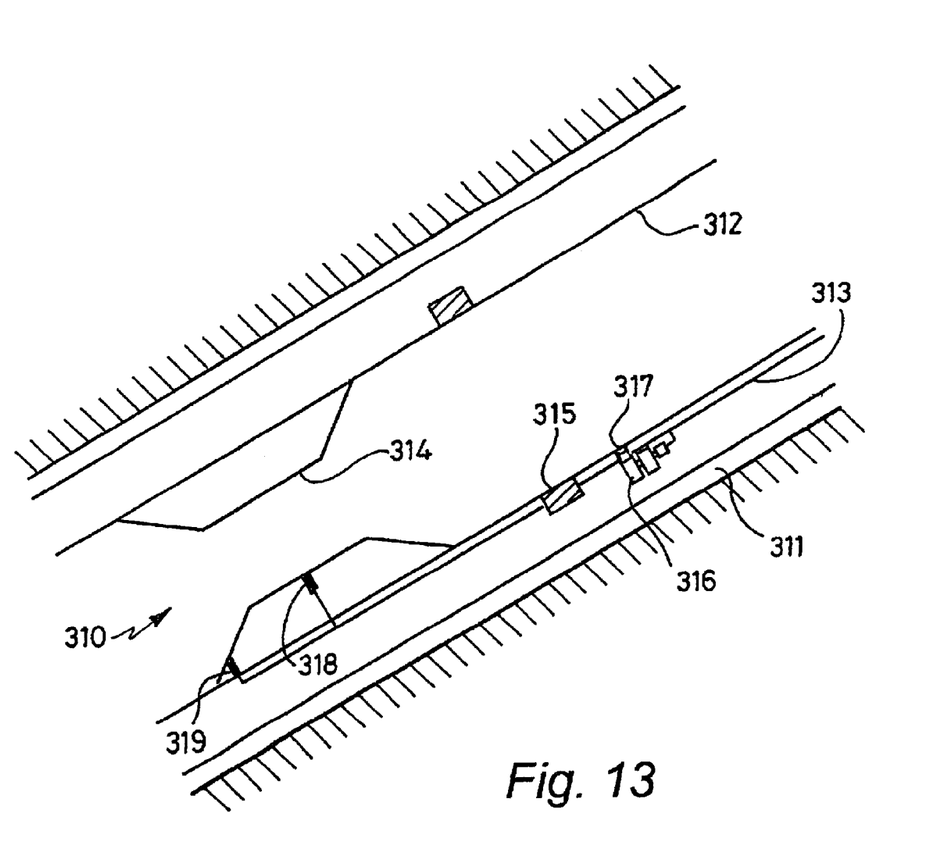
FIG. 13 shows a sensor located downstream of a venturi-type flowmeter, in accordance with the invention.

In FIGS. 11–13 the sensor is shown in various possible downhole applications.

In FIG. 11, there is shown a formation testing apparatus 110 held on a wireline 112 within a wellbore 114. The apparatus 110 is a well-known modular dynamic tester (MDT, Mark of Schlumberger) as described in the co-owned U.S. Pat. No. 3,859,851 to Urbanosky U.S. Pat. No. 3,780,575 to Urbanosky and U.S. Pat. No. 4,994,671 to Safinya et al., with this known tester being modified by introduction of a potentiometric analyzing tool 116 as described in detail above. The modular dynamics tester comprises body 120 approximately 30 m long and containing a main flowline bus or conduit 122. The analysing tool 116 communicates with the flowline 122 via opening 117. In addition to the novel sensor system 116, the testing apparatus comprises an optical fluid analyser 130 within the lower part of the flowline 122. The flow through the flowline 122 is driven by means of a pump 132 located towards the upper end of the flowline 122. Hydraulic arms 134 and counterarms 135 are attached external to the body 120 and carry a sample probe tip 136 for sampling fluid. The base of the probing tip 136 is isolated from the wellbore 114 by an o-ring 140, or other sealing devices (packers).

Before completion of a well, the modular dynamics tester is lowered into the well on the wireline 112. After reaching a target depth, i.e., the layer of the formation which is to be sampled (here: 142), the hydraulic arms 134 are extended to engage the sample probe tip 136 with the formation. The o-ring 140 at the base of the sample probe 136 forms a seal between the side of the wellbore 144 and the formation 142 into which the probe 136 is inserted and prevents the sample probe 136 from acquiring fluid directly from the borehole 114.

Once the sample probe 136 is inserted into the formation 142, an electrical signal is passed down the wireline 112 from the surface so as to start the pump 132 and the sensor systems 116 and 130 to begin sampling of a sample of fluid from the formation 142. The potentiometric detector 116 is adapted to measure the pH and ion-content of the formation effluent.

A bottle (not shown) within the MDT tool may be filled initially with a calibration solution to ensure in-situ (downhole) calibration of sensors. The MDT module may also contain a tank with a greater volume of calibration solution and/or of cleaning solution which may periodically be pumped through the sensor volume for cleaning and re-calibration purposes.

Potentiometric probes in an MDT-type downhole tool may be used for the absolute measurements of downhole parameters which significantly differ from those measured in samples on the surface (such as pH, Eh, dissolved $H_2S$, $CO_2$). This correction of surface values are important for water chemistry model validation.

A further possible application of the novel sensor and separation system is in the field of measurement-while-drilling (MWD). The principle of MWD measurements is known and disclosed in a vast amount of literature, including for example U.S. Pat. No. 5,445,228, entitled "Method and apparatus for formation sampling during the drilling of a hydrocarbon well".

In FIG. 12, there is shown a wellbore 211 and the lower part of a drill string 212 including the bottom-hole-assembly (BHA) 210. The BHA carries at its apex the drill bit 213. It includes further drill collars that are used to mount additional equipment such as a telemetry sub 214 and a sensor sub 215. The telemetry sub provides a telemetry link to the surface, for example via mud-pulse telemetry. The sensor sub includes the novel potentiometric analyzing unit 216 as described above. The analyzing unit 216 collects fluids from the wellbore via a small recess 217 protected from debris and other particles by a metal mesh.

During drilling operation wellbore fluid enters the recess 217 and is subsequently analyzed using sensor unit 216. The results are transmitted from the data acquisition unit to the telemetry unit 214, converted into telemetry signals and transmitted to the surface.

A third application is illustrated in FIG. 13. It shows a venturi-type flowmeter 310, as well known in the industry and described for example in the U.S. Pat. No. 5,736,650. Mounted on production tubing or casing 312, the flowmeter is installed at a location within the well 311 with a wired connection 313 to the surface following known procedures as disclosed for example in the U.S. Pat. No. 5,829,520.

The flowmeter consists essentially of a constriction or throat 314 and two pressure taps 318, 319 located conventionally at the entrance and the position of maximum constriction, respectively. Usually the venturi is combined with a densiometer 315 located further up- or downstream.

The novel potentiometric analyzing unit 316 is preferably located downstream from the venturi to take advantage of the mixing effect the venturi has on the flow. A recess 317 protected by a metal mesh provides an inlet to the unit.

During production wellbore fluid enters the recess 317 and is subsequently analyzed using sensor unit 316. The results are transmitted from the data acquisition unit to the surface via wires 313.

Figure 14:
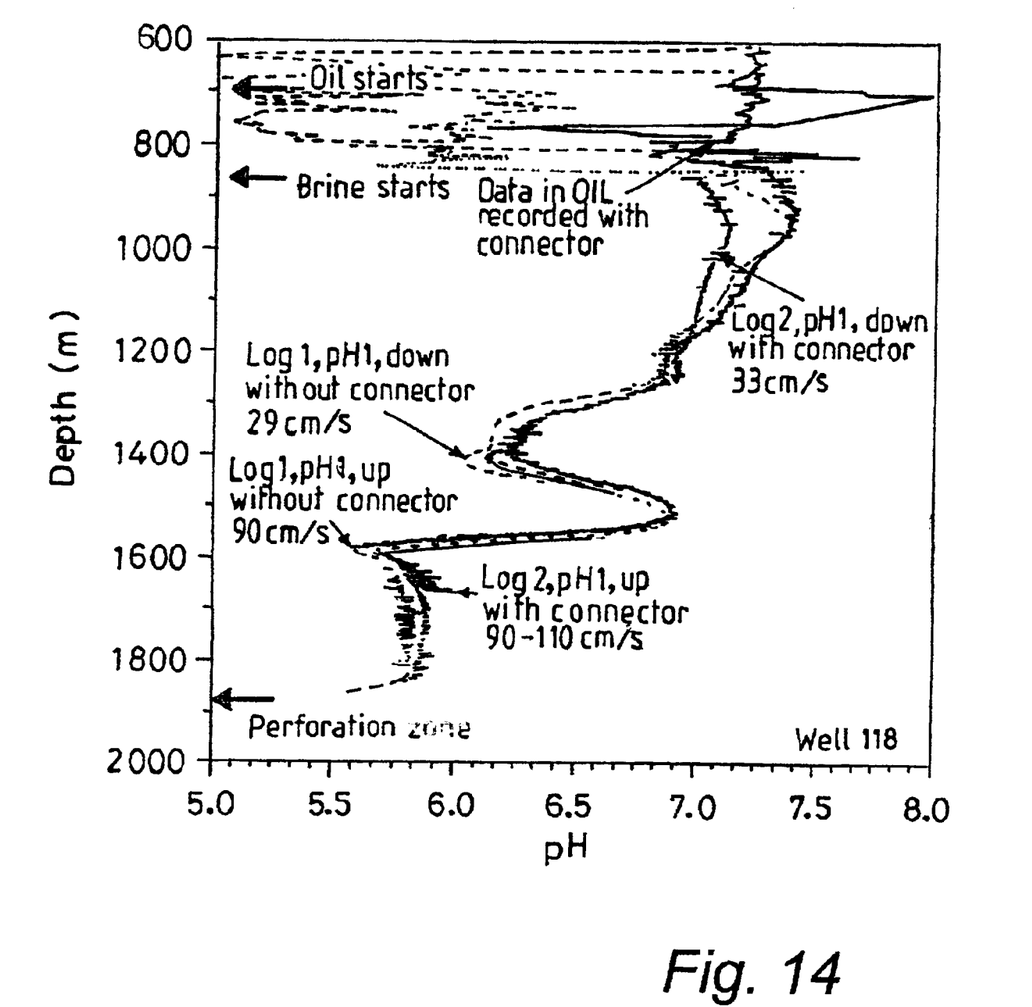
FIG. 14 depicts an example of continuous measurement that has been performed in a shut oil producer, in accordance with the invention.

The above system allows continuous measurements in a water-in-oil emulsion up to 90 vol % of crude oil. An exemplary measurement has been performed in a shut oil producer and is depicted in FIG. 14.

The logs #1 and #2 were recorded using a potentiometric probe as described in FIG. 3. The recording took place after pulling out tubing in a cased well (ID casing 139.7 mm) in the Kazanskoe oilfield, Suhodol area, 120 km north-east from Samara city, Russia.

Log#1 was recorded with separated pH and reference electrodes without water-wet connection between the electrodes. No signal was recorded in oil layer (700–870 m) due to the absence of an electrical contact. In the underlying brine a stable reproducible signal was recorded. This is due the water-wet surface of a glass pH electrode (no oil fouling) and continuous induced discharge of the reference KCl solution out of the reference electrode (no fouling of the reference junction.

Log#2 was recorded with a capillary contact between the reference electrode and the pH glass membrane ("connector"). KCl solution was continuously pushed out of the reference. This ensured a direct discharge of KCl liquid onto glass membrane, i.e. a stable electrical contact in oil. Note that the presence of the connector resulted in reasonable pH values in a layer of nearly pure oil (700–870 m) (red and blue lines). These values roughly correspond to the pH of brine just below oil layer. Note also the good agreement between upwards and downwards logs recorded at different speeds in brine.

The stability of a signal/electrode fouling was checked via measuring a signal with and without an additional resistance as a function of time (see FIG. 9).

Design of new electrodes and use of new combinations of potentiometric electrodes in oil-water mixtures.

A new gas sensing combination is proposed which allows simultaneous determination of partial pressures of $CO_2$ and $H_2S$ in any phase (oil, gas, water). This is a modification of existing gas-sensing combinations. The novelty is that the present invention proposes the use of three electrodes (pH, pS, and reference) in one sensor in order to obtain simultaneously the partial pressures for the above two gases.

Various embodiments of the invention have been described. The descriptions are intended to be illustrative of the present invention. It will be apparent to those skilled in the art that modifications may be made to the invention as described without departing from the scope of the claims set out below.

What is claimed is:

1. A potentiometric sensor comprising
   - at least one reference electrode;
   - at least one measuring electrode with a membrane;
   - at least one connector between said reference electrode and said measuring electrode, wherein said connector provides a continuous conductive path between said reference and said measuring electrode; and
   - a discharge element adapted to release an aqueous solution or gel from said at least one reference electrode onto said membrane of said at least one measuring electrode.

2. A sensor according to claim 1 wherein the connector comprises a porous material.

3. A sensor according to claim 2 wherein the porous material forms a protective layer for the reference electrode.

4. A sensor according to claim 1 wherein the discharge element is self-discharging into a wellbore effluent.

5. A sensor according to claim 1 wherein the discharge element is controlled by an external control unit.

6. A sensor according to claim 1 wherein the membrane is ion-selective.

7. A sensor according to claim 1 wherein the discharge element uses diffusion.

8. A sensor according to claim 1 wherein in operation the discharge element maintains an aqueous continuum between the measuring electrode and the reference electrode in the presence of a wellbore effluent.

9. A downhole tool for measuring characteristic parameter of wellbore effluent comprising a potentiometric sensor having at least one reference electrode;

at least one measuring electrode with a membrane;

at least one connector between said reference electrode and said measuring electrode, wherein said connector provides a continuous conductive path between said reference and said measuring electrode; a discharge element adapted to release an aqueous solution or gel directly from said at least one reference electrode onto said membrane of said at least one measuring electrode; and a sample probe tip with a conduit for sampling fluid, wherein said sensor communicates with said conduit.

10. A downhole tool according to claim 9 wherein the connector comprises a porous material.

11. A downhole tool according to claim 10 wherein the porous material forms a protective layer for the reference electrode.

12. A downhole tool according to claim 9 wherein the discharge element is self-discharging into a wellbore effluent.

13. A downhole tool according to claim 9 wherein the discharge element is controlled by an external control unit.

14. A downhole tool according to claim 9 wherein the membrane is ion-selective.

15. A downhole tool according to claim 9 wherein the discharge element uses diffusion.

16. A downhole tool according to claim 9 wherein in operation the discharge element maintains an aqueous continuum between the measuring electrode and the reference electrode in the presence of the wellbore effluent.

* * * * *